US011554033B2

(12) United States Patent
Kölbel et al.

(10) Patent No.: US 11,554,033 B2
(45) Date of Patent: Jan. 17, 2023

(54) TUBULAR MEDICAL DEVICE

(71) Applicant: VASCUTEK LIMITED, Renfrewshire (GB)

(72) Inventors: Tilo Kölbel, Hamburg (DE); Vincent Nelis, Renfrewshire (GB); Seonaid Nimmo, Renfrewshire (GB)

(73) Assignee: Vascutek Limited, Renfrewshire (GB)

( * ) Notice: Subject to any disclaimer, the term of this patent is extended or adjusted under 35 U.S.C. 154(b) by 369 days.

(21) Appl. No.: 16/595,880

(22) Filed: Oct. 8, 2019

(65) Prior Publication Data
US 2020/0038211 A1 Feb. 6, 2020

Related U.S. Application Data

(63) Continuation of application No. PCT/GB2018/051285, filed on May 11, 2018.

(30) Foreign Application Priority Data

May 17, 2017 (GB) ...................................... 1707929

(51) Int. Cl.
*A61F 2/95* (2013.01)
*A61F 2/954* (2013.01)
(Continued)

(52) U.S. Cl.
CPC ............ *A61F 2/954* (2013.01); *A61F 2/2433* (2013.01); *A61F 2/958* (2013.01); *A61F 2/966* (2013.01);
(Continued)

(58) Field of Classification Search
CPC ........ A61F 2/954; A61F 2/2433; A61F 2/958; A61F 2/966; A61F 2/95;
(Continued)

(56) References Cited

U.S. PATENT DOCUMENTS

| 4,580,568 A | 4/1986 | Gianturco |
| 5,290,305 A | 3/1994 | Inoue |

(Continued)

FOREIGN PATENT DOCUMENTS

| EP | 0855171 A2 | 7/1998 |
| EP | 0880979 A1 | 12/1998 |

(Continued)

OTHER PUBLICATIONS

International Search Report and Written Opinion of the International Searching Authority for International Application No. PCT/GB2018/051285 dated Sep. 11, 2018.

(Continued)

*Primary Examiner* — Erich G Herbermann
(74) *Attorney, Agent, or Firm* — Foley Hoag LLP

(57) ABSTRACT

Apparatus for progressively dilating the lumen of a narrow natural vessel such as an iliac artery and implanting a tubular device enabling access through the dilated lumen to conduct subsequent procedures via the dilated lumen, includes an inflatable integrated balloon locatable at least partially within the tubular device, the tubular device having a length L1 providing a self-expanding tubular body having at least a portion including stents, so that when the integrated balloon is removed the dilated lumen of the natural vessel remains dilated and supported by the tubular device.

10 Claims, 14 Drawing Sheets

(51) Int. Cl.
- *A61F 2/24* (2006.01)
- *A61F 2/958* (2013.01)
- *A61F 2/966* (2013.01)
- A61B 17/00 (2006.01)
- A61F 2/30 (2006.01)

(52) U.S. Cl.
CPC .............. *A61B 2017/00867* (2013.01); *A61F 2002/30579* (2013.01)

(58) Field of Classification Search
CPC ............ A61F 2002/30579; A61F 2/962; A61F 2/97; A61F 2/2427; A61F 2/2418; A61B 2017/00867
See application file for complete search history.

(56) References Cited

U.S. PATENT DOCUMENTS

| | | | |
|---|---|---|---|
| 5,578,072 | A | 11/1996 | Barone et al. |
| 5,591,228 | A * | 1/1997 | Edoga ................ A61F 2/958 |
| | | | 606/198 |
| 5,925,074 | A | 7/1999 | Gingras et al. |
| 6,036,723 | A | 3/2000 | Anidjar et al. |
| 6,203,568 | B1 | 3/2001 | Lombardi et al. |
| 6,635,080 | B1 | 10/2003 | Lauterjung et al. |
| 6,673,103 | B1 | 1/2004 | Golds et al. |
| 6,773,457 | B2 | 8/2004 | Ivancev et al. |
| 6,938,646 | B2 | 9/2005 | Litton |
| 7,780,622 | B2 | 8/2010 | Fitzpatrick et al. |
| 7,901,446 | B2 | 3/2011 | Fitzpatrick et al. |
| 8,088,155 | B1 | 1/2012 | Lauterjung |
| 8,088,159 | B2 | 1/2012 | Lauterjung |
| 8,092,511 | B2 | 1/2012 | Chuter |
| 8,486,129 | B2 | 7/2013 | Lautherjung |
| 8,652,195 | B2 | 2/2014 | Tani |
| 8,652,198 | B2 * | 2/2014 | Andreas ............ A61B 17/12022 |
| | | | 623/1.11 |
| 8,740,971 | B2 | 6/2014 | Iannelli |
| 8,968,389 | B2 | 3/2015 | Greenberg et al. |
| 9,056,002 | B2 | 6/2015 | Tabor |
| 9,398,964 | B2 | 7/2016 | McGee et al. |
| 9,510,936 | B2 | 12/2016 | McDonald et al. |
| 9,622,894 | B2 | 4/2017 | McGee |
| 9,993,329 | B2 | 6/2018 | McDonald et al. |
| 10,137,021 | B2 | 11/2018 | McDonald et al. |
| 10,219,890 | B2 | 3/2019 | Madjarov et al. |
| 10,413,396 | B2 | 9/2019 | Ashton |
| 11,026,823 | B2 | 6/2021 | McDonald et al. |
| 2003/0024527 | A1 | 2/2003 | Ginn |
| 2003/0120263 | A1 * | 6/2003 | Ouriel .............. A61B 17/32056 |
| | | | 606/1 |
| 2003/0130720 | A1 | 7/2003 | DePalma et al. |
| 2003/0176911 | A1 | 9/2003 | Iancea et al. |
| 2004/0117003 | A1 | 6/2004 | Ouriel et al. |
| 2004/0167618 | A1 | 8/2004 | Shaolian et al. |
| 2004/0215315 | A1 * | 10/2004 | Jones ................ A61L 31/16 |
| | | | 623/1.42 |
| 2005/0060029 | A1 | 3/2005 | Le et al. |
| 2005/0075725 | A1 | 4/2005 | Rowe |
| 2005/0137681 | A1 | 6/2005 | Shoemaker et al. |
| 2005/0230956 | A1 | 10/2005 | Igeta |
| 2006/0184226 | A1 | 8/2006 | Austin |
| 2006/0229700 | A1 * | 10/2006 | Acosta ................ A61F 2/958 |
| | | | 623/1.11 |
| 2007/0010873 | A1 | 1/2007 | Neri |
| 2007/0055347 | A1 | 3/2007 | Arbefeuille |
| 2007/0106368 | A1 | 5/2007 | Vonderwalde |
| 2007/0112422 | A1 | 5/2007 | Dehdashtian |
| 2007/0135904 | A1 | 6/2007 | Eidenschink et al. |
| 2007/0168013 | A1 | 7/2007 | Douglas |
| 2007/0208409 | A1 | 9/2007 | Quigley |
| 2008/0082159 | A1 | 4/2008 | Tseng et al. |
| 2008/0147171 | A1 | 6/2008 | Ashton et al. |
| 2008/0188924 | A1 | 8/2008 | Prabhu |
| 2009/0264991 | A1 | 10/2009 | Paul, Jr. et al. |
| 2010/0152835 | A1 | 6/2010 | Orr |
| 2010/0222869 | A1 * | 9/2010 | Delaney .................. A61F 2/06 |
| | | | 623/1.34 |
| 2010/0234937 | A1 | 9/2010 | Wang et al. |
| 2011/0190862 | A1 | 8/2011 | Bashiri et al. |
| 2011/0230956 | A1 | 9/2011 | White |
| 2012/0059448 | A1 | 3/2012 | Parker et al. |
| 2012/0136431 | A1 | 5/2012 | Chen |
| 2012/0158121 | A1 | 6/2012 | Ivancev et al. |
| 2012/0172887 | A1 | 7/2012 | Hatfield |
| 2012/0239136 | A1 | 9/2012 | Bruzzi |
| 2012/0271401 | A1 | 10/2012 | Bruszewski et al. |
| 2012/0277849 | A1 | 11/2012 | Tani et al. |
| 2012/0290068 | A1 * | 11/2012 | Roeder .................. A61F 2/07 |
| | | | 623/1.13 |
| 2013/0131775 | A1 | 5/2013 | Hadley et al. |
| 2013/0166015 | A1 | 6/2013 | Roeder |
| 2013/0218138 | A1 | 8/2013 | Fargahi |
| 2013/0289713 | A1 | 10/2013 | Pearson et al. |
| 2014/0005586 | A1 | 1/2014 | Feinstein |
| 2014/0194970 | A1 | 7/2014 | Chobotov |
| 2014/0200648 | A1 | 7/2014 | Newell et al. |
| 2014/0249617 | A1 | 9/2014 | Argentine et al. |
| 2014/0257452 | A1 | 9/2014 | Slazas et al. |
| 2014/0277332 | A1 | 9/2014 | Slazas et al. |
| 2014/0277345 | A1 | 9/2014 | Havel et al. |
| 2014/0277359 | A1 | 9/2014 | Slazas et al. |
| 2015/0081004 | A1 | 3/2015 | Takahashi et al. |
| 2015/0105819 | A1 | 4/2015 | Becking et al. |
| 2015/0190221 | A1 | 7/2015 | Schaefer et al. |
| 2015/0265444 | A1 | 9/2015 | Kitaoka |
| 2018/0228593 | A1 | 8/2018 | Eaton et al. |
| 2019/0192273 | A1 | 6/2019 | Debus et al. |
| 2019/0223996 | A1 | 7/2019 | McDonald |
| 2020/0038169 | A1 | 2/2020 | Nelis |
| 2020/0038184 | A1 | 2/2020 | McLean |
| 2020/0214821 | A1 | 7/2020 | McDonald |
| 2021/0204954 | A1 | 7/2021 | Nimmo |
| 2021/0212846 | A1 | 7/2021 | Shahriari |
| 2021/0228330 | A1 | 7/2021 | Kelly |
| 2021/0236257 | A1 | 8/2021 | Walzman |
| 2021/0299424 | A1 | 9/2021 | King |
| 2021/0307641 | A1 | 10/2021 | Rumbles et al. |
| 2022/0023080 | A1 | 1/2022 | McDonald |
| 2022/0023081 | A1 | 1/2022 | McDonald |

FOREIGN PATENT DOCUMENTS

| | | | |
|---|---|---|---|
| EP | 1847236 A2 | 10/2007 | |
| EP | 2676639 A1 | 12/2013 | |
| EP | 3115022 A1 | 1/2017 | |
| EP | 3248572 A1 | 11/2017 | |
| EP | 3323385 A1 | 5/2018 | |
| JP | H07308330 A | 11/1995 | |
| WO | WO-2004/064686 A1 | 8/2004 | |
| WO | WO-2006/034340 A1 | 3/2006 | |
| WO | WO-2008/057569 A1 | 5/2008 | |
| WO | WO-2008/088835 A1 | 7/2008 | |
| WO | WO-2008/112270 A1 | 9/2008 | |
| WO | WO-2009/009376 A2 | 1/2009 | |
| WO | WO-2009/082718 A1 | 7/2009 | |
| WO | WO-2009/153768 A1 | 12/2009 | |
| WO | WO-2010/053563 A1 | 5/2010 | |
| WO | 2012164292 A1 | 12/2012 | |
| WO | WO-2012164292 A1 * | 12/2012 | .............. A61F 2/07 |
| WO | WO-2014/096811 A2 | 6/2014 | |
| WO | WO-2014/163957 A1 | 10/2014 | |
| WO | WO-2016075615 A3 | 6/2016 | |
| WO | WO-2017/136733 A1 | 8/2017 | |
| WO | WO-2017/203056 A1 | 11/2017 | |

OTHER PUBLICATIONS

Levack et al., "Rapid Aortic Arch Debranching Using the Gore Hybrid Vascular Graft," Ann Thorac Surg, 95: e163-e165 (2013).

(56) References Cited

OTHER PUBLICATIONS

Nigro et al., "Use of the Gore Hybrid Vascular Graft in a challenging high-lying extracranial carotid artery aneurysm," J Vasc Surg, 59: 817-820 (2014).
Parodi, J.C., et al., "Transfemoral Intraluminal Graft Implantation for Abdominal Aortic Aneurysms," Annals of Vascular Surgery, vol. 5, pp. 491-499 (1991).
Shrestha et al., "Total aortic arch replacement with a novel 4-branched frozen elephant trunk prosthesis: Single-center results of the first 100 patients," Journal of Thoracic and Cardiovascular Surgery, 152(1): 148-159 (2016).

* cited by examiner

TUBULAR MEDICAL DEVICE

This application claims priority benefit from International Application No. PCT/GB2018/051285, filed on May 11, 2018, which claims priority to Great Britain Patent Application No. 1707929.4, filed on May 17, 2017, each of which is incorporated herein by reference in its entirety.

FIELD OF THE INVENTION

This disclosure relates to medical devices, particularly grafts and delivery systems for such grafts for use in treating defective native parts of the vasculature. The disclosure relates to procedures, delivery systems and devices useful in any narrow lumen of a natural vessel but for convenience will be described without limitation in relation to the vasculature where there is a significant and hitherto unmet need for such procedures and devices.

BACKGROUND OF THE INVENTION

Arteries may be subject to stenosis which is an abnormal narrowing of the lumen within the artery over time. Such narrowing may have adverse consequences including blockage of the artery, restricted blood supply to tissue and elevated blood pressure. Iliac arteries in particular present difficulties because they are often tortuous and of narrow lumen dimension, and these arteries in elderly patients are more susceptible to disease or stenosis due to atherosclerosis or calcification. An iliac arterial occlusion may lead to lower extremity issues such as reduced mobility, fatigue or cramp in the legs, and in neglected cases or diabetic patients, to ulcers and tissue necrosis. Surgical interventions, such as revascularization or by-pass surgery may be possible in some cases, but an endovascular procedure, being a minimally invasive procedure, often offers a more effective approach to treatment with less risk for the patient in most cases.

A typical endovascular procedure would be an endovascular aneurysm repair (EVAR). Typically this involves inserting an endograft on a delivery system via a groin incision along a guidewire or catheter inserted into the femoral artery to ultimately access an aneurysmic site, in one of the major vessels of the vasculature. However, such a procedure can be inhibited or prevented if part of the vascular pathway for delivery is occluded, unduly tortuous, or otherwise of limited patency as in the case of stenosis of the iliac artery.

In an endovascular procedure, a manufactured medical device including a tubular form part is inserted into a natural or native vessel forming part of the vasculature as a graft substitute for a diseased or weakened part of the natural vessel, or as a prosthetic support for the diseased or weakened part of the natural vessel.

SUMMARY OF THE INVENTION

The present disclosure relates to endovascular devices which may be useful in treatment of patients suffering from defects and weaknesses in the vasculature, and is particularly intended for those patients requiring treatment for stenosis of the natural iliac vessels including the common iliac, internal and external iliac arteries.

The iliac arteries are usually of small lumen diameter, thereby providing limited intravascular access and requiring a low profile device to accomplish an endovascular procedure. Such a procedure often entails use of an introducer sheath which guides catheters, introducer or access guidewires, and delivers devices into the target site within the vasculature. It would be an objective of such an endovascular procedure to insert a tubular device to provide a bypass bridging the diseased or weak part of the artery and to provide a substitute lumen between remaining healthy parts of the artery to allow throughflow of blood. However, it has been observed that the iliac arteries are particularly susceptible to damage such as a sheath-induced laceration. It is not unknown for removal of the introducer sheath to unintentionally rupture an iliac artery or expose a rupturable weakness by avulsion. Therefore access to deliver a device to a target site within the vasculature via the natural iliac vessels is challenging.

Such a tubular device is typically made from a physiologically acceptable woven fabric formed into a tubular sleeve. The tubular sleeve would be delivered in a collapsed or compact configuration within a delivery system, and may be expanded at the target site using an expandable balloon device or enclosed resilient stents which can provide support to the tubular sleeve and maintain the lumen thereof open to allow fluid flow through the tubular sleeve.

Due to the anticipated limited access to and through natural iliac vessels, a preliminary stage of assessment by imaging and preparation for implanting a suitable graft may indicate that appropriate treatment requires successive dilation steps each progressively aiming to achieve an enlargement of the target vessel in order to improve access through and beyond the target vessel. Dilation is achievable by use of inflatable balloon devices. However insertion of such balloon devices into vessels of the vasculature requires use of multiple introducer sheaths/catheters which are also to be successively inserted and removed, which actions can damage the walls of the penetrated vessels. Even in the case of careful dilation, the expansion achievable may be insufficient to permit access for the intended graft and its associated delivery system. In such cases an intentional rupture of the target vessel by a surgical incision may still be necessary.

It would be of benefit if at least some of these difficulties could be alleviated or mitigated.

The present disclosure relates to apparatus for dilating the lumen of a natural vessel and implanting a tubular device to provide access through the dilated lumen of the natural vessel, thereby enabling access for subsequent procedures via the dilated lumen with reduced risk of an adverse event due to manipulation of devices through the lumen of the natural vessel.

The apparatus for dilating the lumen of a natural vessel may comprise a dilation device comprising a removable expansion component such as an inflatable balloon, and a dilated lumen support component such as a self-expanding tubular body having at least a portion thereof that is stented, so that when the expansion component is removed the dilated lumen of the natural vessel remains dilated due to the remaining lumen support component.

The natural vessel may be part of the vasculature, especially a narrow or tortuous natural vessel such as an iliac artery. This disclosure therefore also relates to an improved endovascular dilation device of tubular form, a delivery system for that endovascular dilation tubular device and a procedure for dealing with problems associated with tortuous and narrow lumen natural vessels of the vasculature. The implanted endovascular dilation device is expandable from an initially compact configuration within a removable sheath to provide access for subsequent endovascular procedures such as advancement of devices, implements and materials to another treatment site beyond the implanted endovascular dilation device of tubular form.

The presently disclosed delivery system for a tubular device, for example, an endovascular tubular device includes a delivery shaft and an integrated balloon which is also in compact form within the tubular device and deliverable within the endovascular dilation device in compact form within the removable sheath. In an embodiment of a typical use of the system and tubular device, both the tubular device which is expandable and the integrated balloon used to initiate dilation of the natural vessel, would be delivered at the same time on the same delivery shaft in compact form within a removable sheath. Since the tubular device includes a self-expanding tubular body having at least a portion thereof that is stented, when the removable sheath is removed, the tubular device will tend to expand immediately and will be limited only by the extent that the natural vessel has been dilated by inflation of the integrated balloon. Thus, in use, an endovascular lumen dilation of a natural vessel is initiated by the integrated balloon, and maintained by the tubular device when the integrated balloon is removed.

The endovascular tubular device may comprise a fabric sleeve and a plurality of ring stents attached to at least a length portion of the fabric sleeve.

Expansion of the natural vessel lumen dimension using a dilation device may be accomplished in successive steps; firstly by expansion of the integrated balloon, and subsequently by removal of the integrated balloon on its delivery shaft, and insertion of at least one further delivery shaft bearing a balloon that has greater expansion capability. It will be understood that in a narrow, fine and possibly tortuous lumen of a natural vessel, care has to be taken to avoid an adverse event during the desired widening of the lumen. A cautious approach using multiple balloons of increasing expansion capability in successive steps minimises the risks associated with the intricate procedure required.

Apparatus for accomplishing this successive dilation procedure may be in the form of a kit comprising an expandable tubular device, a delivery system including a delivery shaft with an integrated balloon, and a plurality of expandable balloons of increasing expandable size and which are respectively deliverable on a delivery shaft after the integrated balloon has been used and withdrawn. In this way, the tortuous and narrow lumen natural vessel may be dilated in successive steps until an acceptable lumen dimension suitable for through delivery of a device on a delivery system such as would be required for any endovascular (such as EVAR, TEVAR, TAVR and modifications thereof etc.) procedure. Even if it is necessary to crack open the tortuous and narrow lumen natural vessel to obtain adequate access, the tubular device present throughout the dilation procedure serves as a substitute for the cracked part of the natural vessel and remains resident after the dilation procedure to bridge the cracked part of the dilated natural vessel and thereby provide a continuous lumen through which devices may be delivered and procedures carried out. Thus it will be understood that the present disclosure provides access via a natural lumen that would otherwise be difficult to use without an open surgical intervention, and offers strengthening or substitution for the tortuous and narrow lumen with the aim, for example, of pursuing an endovascular procedure without requiring an open surgical intervention at the site of the tortuous and narrow lumen natural vessel.

In embodiments, the tubular device used to support the dilated natural vessel, and maintain the patency of the dilated natural vessel may be a wholly endoluminal tubular body incorporating stents including self-expanding stents, for example made from a shape memory material.

In some alternative embodiments, the tubular device used to support the dilated natural vessel, and maintain the patency of the dilated natural vessel may be a wholly endoluminal tubular body that is expanded passively under the control of the balloon(s) used for dilating the natural vessel.

In embodiments the tubular device used to support the dilated natural vessel, and maintain the patency of the dilated natural vessel may be a hybrid device where only a length portion of the tubular device is an endoluminal tubular body incorporating stents including self-expanding stents, for example made from a shape memory material.

In embodiments, an apparatus in kit form suitable for an endovascular purpose includes an endovascular dilation device comprising in combination a tubular body that is configured for insertion into a lumen of a natural vessel of the vasculature in a compact form within a removable sheath; and a delivery system comprising a delivery shaft and an integrated balloon that is also configured for insertion into a lumen of a natural vessel of the vasculature in a compact form within the same removable sheath, wherein the integrated balloon is one that is undersized in relation to the maximum potential expanded dimension of the tubular body; and a plurality of expandable balloons of differing expandable size for successive use in expanding the tubular body, each expandable balloon being insertable in turn into the lumen in a compact form upon a delivery shaft for use in progressively dilating the lumen of the natural vessel of the vasculature. The kit may comprise a malleable delivery shaft, a flexible delivery shaft and optionally a guide wire or catheter.

Since the tubular body which expands at the same time as the integrated balloon, or any subsequent balloon, is used to dilate the lumen of the natural vessel, it prevents the natural vessel collapsing after the removal of the balloon(s) and maintains the patency of the dilated lumen of the natural vessel. Alternatively, it can be considered that the integrated balloon acts through the tubular body so that the combination serves as an endovascular dilation device in an endoluminal dilation apparatus.

In embodiments the tubular body may be entirely compacted within a removable sheath for delivery with the integrated balloon on a delivery shaft, and the tubular body may be configured to be entirely placed by an endovascular procedure. The tubular body may be fully stented with a sufficient number of self-expanding stents located throughout its length so that after the endovascular placement procedure the tubular body is fully self-deployed when the delivery system and any lumen dilating balloon is removed.

A tubular device suitable for use as an endovascular dilation device as disclosed herein comprises a tubular body that is configured for insertion into a lumen of a natural vessel of the vasculature in a compact form within a removable sheath, wherein the tubular body has a length L wherein at least one tubular length portion L' thereof is initially sheathed and subsequently expandable within the lumen of the natural vessel of the vasculature, and wherein at least one further tubular length portion $L^2$ is positioned upon a resilient support so that the resilient support is usable to position the tubular body such that the tubular length $L^1$ of said tubular body is positionable within the lumen of the natural vessel and releasable from the removable sheath to provide an open lumen within the lumen of the natural vessel of the vasculature.

The resilient support may comprise an elongate catheter, an elongate flexible shaft, or an elongate guide wire. A malleable material may be used for the resilient support, such as to form a metal rod, or a metal rod or coil co-extruded with a flexible polymer resin or flexible composite resin coating, to form a delivery shaft which can be shaped by a user during a procedure to aid positioning or access to a portion of the natural vessel or tissue adjacent the natural vessel. The malleable material may be a metallic material for example stainless steel or a shape-memory metallic alloy.

In embodiments the tubular length portion $L^2$ has an internal valve providing a fluid-tight seal around an elongate catheter, elongate flexible shaft or elongate guide wire forming part of or associated with a delivery system for the tubular device. The tubular length portion $L^2$ provides an access route for the delivery systems required in the endovascular steps of a surgical procedure intended for repairing a deteriorated part of a natural vessel, for example a vessel of the vasculature.

Optionally, an external tool may be used to clamp the length portion $L^2$ to provide fluid flow control, for example, as a haemostatic valve or stopper to minimise blood loss during any stage of the procedure, such as placement, deployment or manipulation of devices in or through the tubular body in the natural vessel being treated.

The tubular length portion $L^2$ does not require provision of any internal supports such as stents throughout its length, but may comprise a corrugated, or crimped sleeve of fluid-impermeable or negligible-permeability fabric.

The unstented tubular length portion $L^2$ may have tabs or ribbon loops attached to an outer surface to improve handling.

In embodiments the length portion $L^2$ may be significantly shorter than the tubular length $L^1$ which is positionable within the lumen of the natural vessel.

When suitably compacted within a sheath in a delivery system or delivery device, the external width dimension to fit within a lumen of a natural vessel may be in the range of from 3 mm to 6 mm. In embodiments, a tubular device and the sheath used to maintain the tubular device in a compact form for delivery into a lumen of natural vessel may be in the range of from about 6 to 18 French.

The removable sheath may be made from a physiologically benign low friction or slip polymeric material such as polytetrafluoroethylene (PTFE). The removable sheath may alternatively be formed from polyethyleneterephthalate (PET). The selected material should be one which is biocompatible and may be readily passed through natural vessels or artificial lumens without sticking. The removable sheath may be surface treated, for example to impart or enhance hydrophilic properties by applying a hydrophilic coating.

Suitable polymeric flexible materials for the removable sheath may be selected from thermoplastic polymers, elastomers, and copolymers such as nylon, polyurethane, polyethylene (PE), polytetrafluoroethylene (PTFE), expanded polytetrafluoroethylene (ePTFE), fluorinated ethylene propylene, polyether block amides (PEBA), polyimide, polyether ether ketone, and polybutylene terephthalate.

The sheath may be removable by pulling using a handle, draw wire or strap attached to the sheath.

The sheath may be designed to split (for example tear) in a predictable and controllable manner under application of appropriately applied force. Such force can be applied using a slitting tool which may be incorporated in the delivery system. By application of such force, the sheath may tear along its length and separate to release tubular body.

In embodiments the splittable sheath is retractable against a hub comprising a splitter mechanism to facilitate removal of the retracted sheath from the stented tubular part after deployment within the natural vessel.

In embodiments the splitter mechanism may comprise one or more passive (static) slitter elements disposed to present slitter blade edges in the proximal-distal axial direction of the tubular body whereby the sheath becomes split by retraction against these slitter blade edges of the passive slitter element(s).

In embodiments the splitter mechanism may comprise at least a pair of slitter elements which may be provided upon or within the hub The splitter mechanism may separate the splittable sheath in one or more places, forming at least one longitudinal slit such that the sheath is removable in one piece, or optionally in more than one piece, for example split longitudinally into halves.

The slitter elements may be made of a plastics material such as a polyamide, for example a nylon.

In alternative embodiments the splittable sheath is designed to be peeled or pulled apart by incorporating tear lines, perforations, pre-cut parts, or introducing sutures which facilitate separation in a controlled manner.

An option for such an embodiment is to provide a fine pull strand that is retrievable, passes within the splittable sheath and is attached at the distal end of the splittable sheath, for example by a suture, the pull strand returning over the splittable sheath to the proximal end, and which is thin enough to split the splittable sheath as it is withdrawn over the splittable sheath. A user pulling upon the pull strand externally from the proximal end of the pull strand lifts the distal end of the pull strand and causes the pull strand to begin splitting the splittable sheath. Continued external pull upon the pull strand by a user splits the splittable sheath from distal to proximal end. The proximal end of the splittable sheath may be attached to a pull wire or pull strap for retrieval of the split sheath.

The tubular body when released into the target natural vessel forms a restored lumen for blood flow and facilitates passage of devices through the natural vessel.

The length portion $L^1$ of the tubular body may be formed of a material that is expandable permanently to retain the expanded dimensions after an expansion step.

In embodiments, the length portion $L^1$ of the tubular body may be formed of expanded polytetrafluoroethylene (ePTFE) or a polyester fabric.

Any physiologically inert or benign material such as a polyester may be used to form a tubular body that is substantially impermeable to fluids, including air, and bodily fluids.

Prosthetic grafts normally used for such replacement are typically made from polyester fabric, which may be woven or knitted, and may be sealed with a sealant, for example gelatine or collagen.

The tubular body may be made of a fabric (usually a knitted or woven fabric) of ePTFE, PTFE or polyester, polyethylene or polypropylene and may optionally be coated to reduce friction; discourage clotting or to deliver a pharmaceutical agent. The fabric will generally be porous on at least one surface to enable cell ingrowth.

The length portion $L^1$ of the tubular body may be expanded when using a balloon device to dilate the lumen of a natural vessel. Balloon devices are known in the art as for example mentioned in U.S. Pat. No. 5,925,074A, EP0855171A2 and EP2676639A1. A balloon device representative of suitable devices is available from Atrium International. Typically a balloon normally used for expansion of a device, such as a balloon expandable graft to be presented upon a delivery shaft or catheter, has a collapsible tubular shape with tapering ends. The tubular shape may thus present truncated cone-shaped tapered sections on the distal and proximal ends of a straight tubular profile section, which tapered sections may overlie or be fixed to tubular elements and usually admit through passage of a delivery wire, shaft or catheter within such a tubular element. The straight tubular profile section may be expanded into a hollow cylindrical shape. A balloon-expandable device such as a graft would be mounted onto the outside surface of the straight tube section. Such a device is useful for the purpose of dilating the lumen of a constricted natural vessel in conjunction with deployment of the tubular body disclosed herein to provide a clear passage for access beyond the site of the constriction in the natural vessel.

The length portion $L^1$ of the tubular body may be designed to receive a balloon associated with a delivery system, which balloon is removable with the latter. The balloon may be an integrated part of the delivery system such that, a device, for example a tubular body graft with a balloon expandable component, the delivery system for that device, and the balloon, together as an assembly connected by a release wire, are inserted into the patient. The delivery system and balloon are subsequently removed after delivery, deployment and release of the device.

The length portion $L^1$ of the tubular body may be supported in an expanded profile by one or more stent elements, whereby the increased lumen width dimension is preserved after the balloon is removed. The length portion $L^1$ may be described hereinafter as the "endo-section", as it is a portion of the tubular body that is insertable first into the lumen of a natural vessel.

The stent elements may comprise ring stents, at least some of which may be saddle shaped. Suitable stents are disclosed in WO2012/164292 A1.

The length portion L' of the tubular body may be expandable to a width dimension that exceeds the size of the lumen of a normal natural vessel, i.e. a native vessel that is not constricted, diseased, weakened or subject to stenosis. The length portion L' of the tubular body may be used to expand an iliac vessel and provide a reinforcement graft within the iliac vessel. Such a reinforcement graft offers protection to a fragile vessel such as the iliac and provides an opportunity to subsequently pass through items such as a delivery system, a component such as a balloon to permit further expansion, or a graft.

In embodiments, the length portion $L^1$ of the tubular body may be expandable to a width dimension in the range of from 6 mm to 14 mm.

In use, with respect to a user of the tubular device, the length portion $L^1$ of the tubular body is a distal portion.

The open lumen of the length portion $L^2$ may be of at least substantially equivalent size to the lumen of a normal natural vessel, i.e. a native vessel that is not constricted, diseased, weakened or subject to stenosis, and dimensioned to admit a delivery system component or compact device to pass through it. The open lumen of the length portion $L^2$ may have a width dimension in the range of from 6 mm to 14 mm.

In use, with respect to a user of the tubular device, the length portion $L^2$ of the tubular body is a proximal portion.

The tubular body may be of a material that is resistant to abrasion or physical contacts arising from repeated passage of a delivery system component through the lumen of the tubular body as for example in a typical EVAR procedure. The material may be designed to withstand at least 3, or 4, or 5, or more successive procedures to insert and withdraw a delivery system component through the lumen of the tubular body.

Suitable materials include expanded polytetrafluoroethylene (ePTFE) or a polyester fabric.

Any physiologically inert or benign material such as a polyester may be used.

Prosthetic grafts normally used for such replacement are typically made from polyester fabric, which may be woven or knitted, and may be sealed with a sealant, for example gelatine or collagen.

The tubular body may be made of a fabric (usually a knitted or woven fabric) of ePTFE, PTFE or polyester, polyethylene or polypropylene and may optionally be coated to reduce friction; discourage clotting or to deliver a pharmaceutical agent. The fabric may be porous on at least one surface to enable cell ingrowth.

In embodiments the material may be a polyester fabric, which may be woven or knitted, and may be sealed with a sealant, for example gelatine or collagen.

At least a part of the material forming the tubular body may be crimped or pleated. Use of a crimped fabric sleeve to form at least a portion of the tubular body provides for its adjustable length, enabling the tubular body to be stretched lengthwise, and when required curved in a desired direction.

The term "crimped" as used in the present disclosure relates to a fabric profile having a circumferential corrugation or spiral profile which when viewed from a side has a generally zig-zag outline or sinusoidal profile wherein the exterior surface undulates from a maximum dimension to a minimum dimension repeatedly over a substantial length of the crimped portion of the tubular body. Such a crimped profile permits additional length for the crimped portion of the tubular body to be obtained by applying a longitudinal stretch. Alternatively a reduced length can be obtained by applying a longitudinal compression. Additionally the crimp surface also accommodates bending of the crimped portion to accommodate re-direction of the tubular body from a straight profile to a curved profile which may be required for connection with a native vessel and to account for vascular variance in patients.

In embodiments, a portion of the tubular body has a length comprising a series of sections, each section having a tab which may be gripped to facilitate trimming of the length of that portion of the tubular body.

In embodiments each section has a holding loop instead of a tab which improves the ability to grasp and hold the tubular body for trimming under the slippery conditions of the surgical procedure due to the presence of body fluids.

The tab or loop can be made of a biocompatible material which may the same as of different from the material used for the tubular body.

In embodiments, the tubular body may be lined or coated internally with a low friction or slip-promoting material to facilitate passage of delivery system components or devices through the tubular body. A PTFE liner, coating or layer may be suitable for this purpose.

The thickness of the material forming the tubular body may be in the range of from 0.05 mm to 1.0 mm, preferably 0.7 mm±0.2 mm.

The tubular body may be at least in part supported by a resilient support which may be a stent or a series of stent elements. Suitable stent types may be ring stents but spiral, Z- or zig-zag, and tubular mesh types and combinations of any of these types with or without ring stents may also be suitable.

In embodiments, the tubular body has a length L wherein the at least one length portion $L^2$ thereof is not supported by stents, and the at least one further length portion $L^1$ is supported externally or internally by stents. The stents may be self-expanding stents. The stents may be made of a shape memory material.

In embodiments, the tubular body has a length L wherein the at least one length portion $L^1$ thereof is shorter than the at least one further length portion $L^2$.

In embodiments, the tubular body has a length L wherein the at least one length portion $L^1$ thereof is longer than the at least one further length portion $L^2$.

In embodiments, the tubular body has a length L wherein the at least one length portion $L^1$ thereof is approximately the same length as the at least one further length portion $L^2$.

In embodiments at least a portion of the tubular body is tapered.

In embodiments, the at least one further length portion $L^2$ is tapered to match the natural vessel width dimension.

In embodiments, the tubular body has a length L comprising the at least one length portion $L^1$, the at least one further length portion $L^2$ and at least one length portion $L^3$ which is configured to introduce a curvature, for example pleated fabric material that is optionally stitched to retain the degree of curvature required. In embodiments the at least one length portion $L^3$ is located between the at least one length portion $L^1$ and the at least one length portion $L^2$. In embodiments the at least one length portion $L^3$ is located between the at least one length portion $L^1$ and at least one further length portion of the $L^1$ type.

In embodiments the tubular body comprises at each end of its total length L a length portion of the $L^2$ type and the total length L is made up with at least one length portion $L^1$ therebetween; or, the tubular body comprises at each end of its total length L a length portion of the of the $L^2$ type and the total length L is made up with at least one length portion $L^1$ and at least one length portion $L^3$ in alternate succession, so that the overall length L includes at least one expandable portion and at least one curve.

The tubular body may be provided with a perfusion branch extending laterally from the tubular body.

The perfusion branch may be formed of a fabric attached to the tubular body to form overall a bifurcated "Y" configuration. The perfusion branch may be made a material which is the same as that used to form the tubular body. The perfusion branch may be anastomosed to a natural vessel in the performance of a surgical procedure.

In use the tubular body remains resident in the target natural vessel requiring expansion or dilation or removal of an occlusion or lumen restriction for access, so as to act as an enduring reinforcement to the typically fragile natural vessel. In this way subsequent access for additional procedures or interventions is facilitated with reduced risk of damage to the accessible target natural vessel.

A subsequent endovascular aneurysm repair (EVAR) for example to treat a diseased or malfunctioning part of the aorta may be conducted via the resident tubular body with reduced risk of damaging the natural vessel in which the resident tubular body is located.

Notably the said tubular body once deployed within the target natural vessel can be expanded to a larger lumen dimension in successive natural vessel dilation steps in a sequence using different balloon expansion devices of ever greater inflation capability. In embodiments the tubular body has self-expanding stents, and once the delivery sheath is removed, is only restrained by the confines of the natural vessel. In this way as the balloon expansion device dilates the natural vessel the tubular body retains an expanded dimension due to the support from the self-expanding stents.

Thus the expansion procedure using a balloon within the expandable tubular body to enlarge the natural vessel can be repeated more than once to achieve a desired lumen dimension. In a first step the delivery system with integrated balloon is used to create an initial enlargement of the natural vessel dimension, and also position and deploy a supportive tubular body to maintain the initial enlargement of the natural vessel. Where the initial enlargement of the natural vessel dimension is insufficient for a desired subsequent EVAR procedure, the delivery system with integrated balloon is removed, and another balloon of greater expansion capability is introduced on a delivery system and inflated to cause a second enlargement of the natural vessel. This step can be repeated again to achieve a desired lumen dimension. In some circumstances it may be desired or even necessary to crack a severely damaged or occluded natural vessel such as the iliac, and to sufficiently enlarge a tubular body of a desired lumen dimension to admit an EVAR delivery system. The enlarged tubular body remains resident within the enlarged or cracked natural vessel to substitute for the damaged part and maintain patency of the lumen.

A hand-held delivery system for the presently disclosed tubular device may comprise an elongate, malleable, "delivery" shaft, (or a functional equivalent such as a catheter or wire) upon which the tubular device is borne and deliverable. The delivery shaft may be inserted in a lumen of the tubular device, via the unstented section (tubular length portion $L^2$). The delivery shaft may pass through an introducer dry-seal/valve to inhibit bodily fluid leakage and air ingress.

The elongate, malleable delivery shaft may have an integrated balloon mounted thereon.

In use a tubular body to be used as an endovascular dilation device is located over the integrated balloon upon the elongate, malleable delivery shaft and the device and balloon are restrained in a low-profile compact deliverable form by applying a removable sheath over the device and balloon.

The delivery system may further comprise a user manoeuvring control handle attached to one end of the elongate delivery shaft remote from the distal tip to allow a user to move, manipulate and control the positioning of the delivery system, and the deployment of the tubular device to be deployed therefrom.

The handle may comprise a slotted housing configured to fit over and around the elongate delivery shaft upon which a device may be mounted and constrained in a compact form within a removable sheath, the slotted housing covering at least a part of the tubular device when positioned upon the delivery shaft.

The removable sheath may be split during removal to part the sheath longitudinally, for example along a predetermined tear line, which may be perforated, or slit or cut by contact with a slitter element or cutter blade as the removable sheath is pulled using a puller.

An embodiment of a delivery system may comprise a sheath removal mechanism which includes at least one slitter element for parting the sheath longitudinally to allow the constrained stented tubular part of the endo-section of the tubular device to expand into its deployed configuration, and a sheath removal element, such as a pull strap, cord, tape, wire or the like, connected to the sheath to allow removal of the sheath. The sheath may be slit whenever the pull strap is pulled to bring the sheath into contact with the slitter element The slitter element may permit linear equal splitting of a sheath.

The slitter element may be fixed to or located within a hub that is removably mounted upon an elongate malleable delivery shaft.

The hub may comprise two part-cylindrical parts adapted to fit around the elongate delivery shaft (and guide wire when used) and be clipped or removably fastened together.

In embodiments the hub may have protruding parts formed to have a slitting edge to provide a slitter element for splitting the sheath during retraction of the sheath to allow deployment of the stented tubular part of the endoprosthetic device.

The hub may have a pair of slits through which a pull strap connected on either side of the tail of the sheath can be passed to a pull handle for use by a user for removal of the sheath.

BRIEF DESCRIPTION OF THE DRAWINGS

In the following description additional detail of embodiments will be described by way of illustrative example with reference to the accompanying drawings.

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
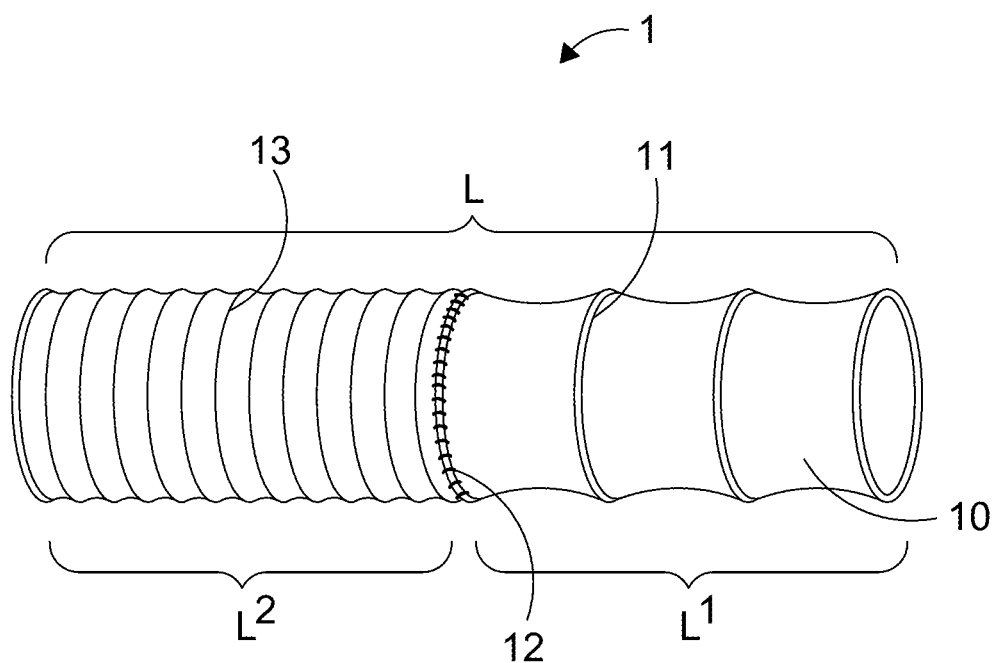
FIG. 1 shows a side view of an implantable tubular body comprising a stented endo-section connected to an unstented section.
Figure 2:
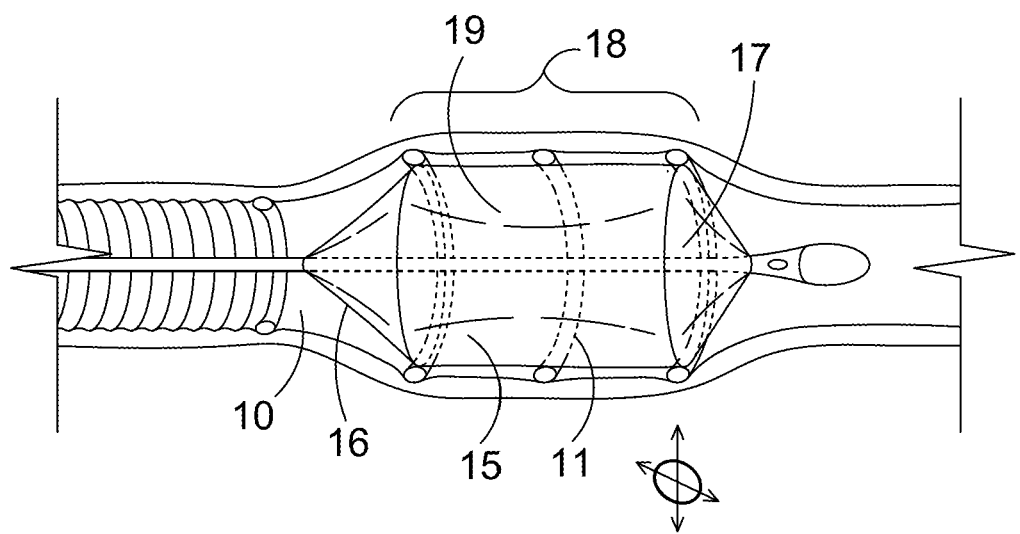
FIG. 2 shows a side view of the implantable tubular body shown in FIG. 1 after the stented endo-section has been expanded using a balloon dilator.

In the embodiment illustrated in FIGS. 1 and 2, an implantable graft comprises two tubular sections secured together for example by sutures 12 to form a blood-tight seal and forming a hollow tubular body 1 having a length dimension L comprising a tubular length portion $L^1$ and a further tubular length portion $L^2$. The tubular length portion $L^1$ forms an endovascular section 10 and has a plurality of stents 11 which are compressible to a compact form and expandable to support the tubular length $L^1$ in an expanded (dilated) configuration. The compact form can be held for delivery by use of a removable sheath.

The implantable graft is made of fabric in the form of a collapsible sleeve, at least part of which 13 may be crimped or pleated. The tubular length portion $L^1$ and the further tubular length portion $L^2$ respectively may be made of the same or different fluid-impermeable fabrics selected from physiologically acceptable or benign materials such as a knitted or woven fabric of ePTFE, PTFE or polyester, polyethylene or polypropylene. The fabric may be sealed with a sealant, for example gelatine or collagen.

The stents 11 are separate deformable ring stents which are individually attached to the fabric sleeve. At least some of these stents 11, optionally all, may be made from a shape-memory metallic or plastics material so as to be self-expanding. Each of the ring stents 11 may be made of continuous loop of resilient material such as stainless steel, or a shape memory metal alloy like nitinol (a nickel-titanium alloy) or high modulus polymers such as polyether ether ketone PEEK or the like, and may be attached to the endovascular section 10 by way of sutures, adhesive or heat bonding as appropriate. Each ring stent 11 may be formed from a shape memory material which may be heat set against the external surface of the endovascular section 10. In the depicted example, the undulating contour of each ring stent 11 comprises a compressible memory material readily forming two peaks 20 and two valleys 22 to form in use a " " saddle-shaped" ring stent. Use of a continuous loop of multiple windings of nitinol wire is advantageous for this purpose A suitable delivery system for the implantable graft disclosed herein includes an integrated balloon dilator for inter alia assisting expansion of the unsheathed endovascular section 10, and at least initiating dilation of the natural vessel. An example of a balloon 15, has a collapsible tubular shape with tapering ends. The tubular shape has truncated cone-shaped tapered sections 16, 17 respectively on the distal and proximal ends of a straight tubular profile section 18, which tapered sections 16, 17 are fixed to a tubular element 19 to define therebetween an expansion volume which may at its fullest extent of expansion exceed the initial natural volume of the corresponding length of the narrow lumen target natural vessel.

The narrow lumen target natural vessel may be a part of the vasculature that is naturally narrow and tortuous such as the iliac arteries, or any natural vessel lumen constricted by stenosis, stricture or calcification.

In use of this embodiment, the implantable graft overlies the integrated balloon 15 sufficiently to be expandable during inflation to provide support to a lumen of a natural vessel dilated at least partially by the integrated balloon, and packaged for delivery within a removable sheath, particularly such that the endovascular section 10 would be compactly sheathed for delivery into a target narrow natural vessel of the vasculature and unsheathed using a release strap or wire attached to the sheath when at least the endovascular section 10 is located in position within the target natural vessel. After removal of the sheath, the balloon 15 would be inflated within the expanding or partially expanded endovascular section 10 so as to dilate the natural vessel to at least a first extent.

Where additional dilation is required, for example to admit an EVAR system, the delivery system and integrated balloon dilator would be withdrawn and another balloon of greater dilation capacity would be delivered on a suitable further delivery system, inflated to further dilate the natural vessel and permit additional expansion of the endovascular section 10 and then that further delivery system and balloon would be removed after deflation of the balloon. The procedure can be repeated by substitution of further balloons until the natural vessel is fully dilated, or event ruptured whilst the fully expanded endovascular section serves as an implantable graft lumen of a desired lumen patency.

Figure 3:
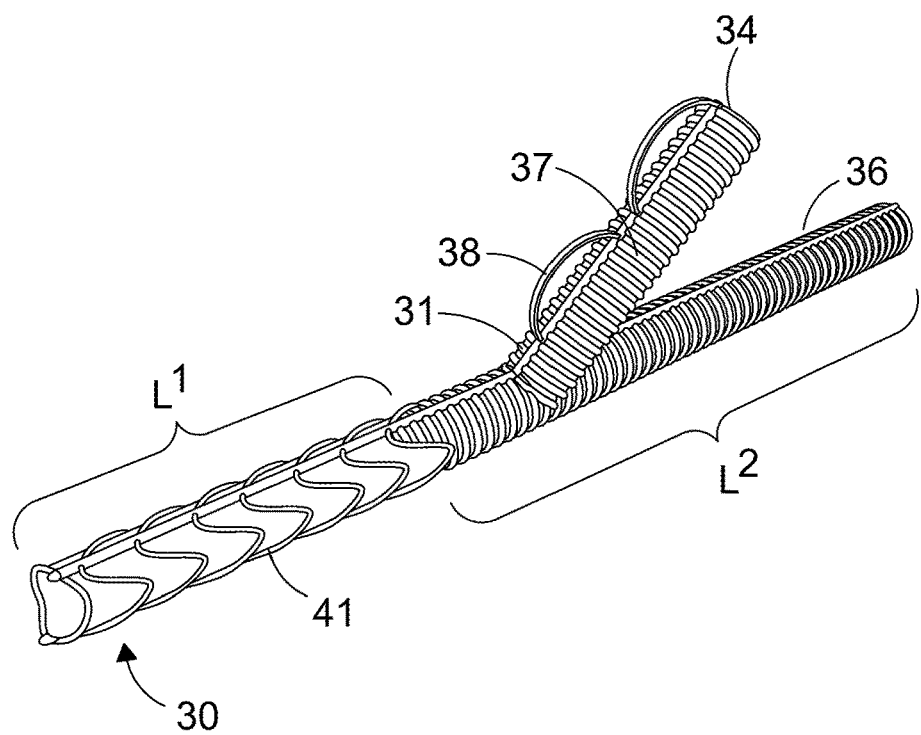
FIG. 3 is a view from above and to one side of another embodiment of an implantable tubular body.
Figure 4:
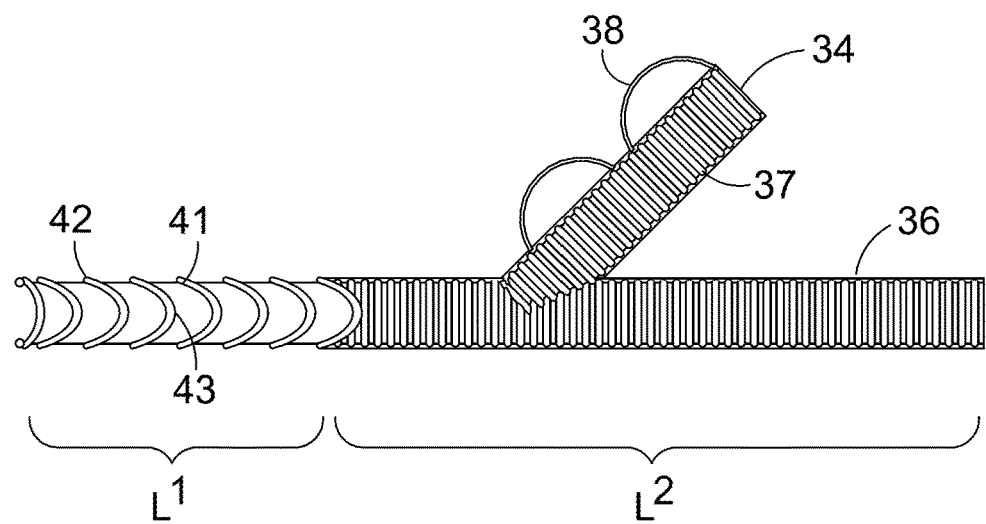
FIG. 4 is a view from one side of the implantable tubular body of FIG. 3.
Figure 5:
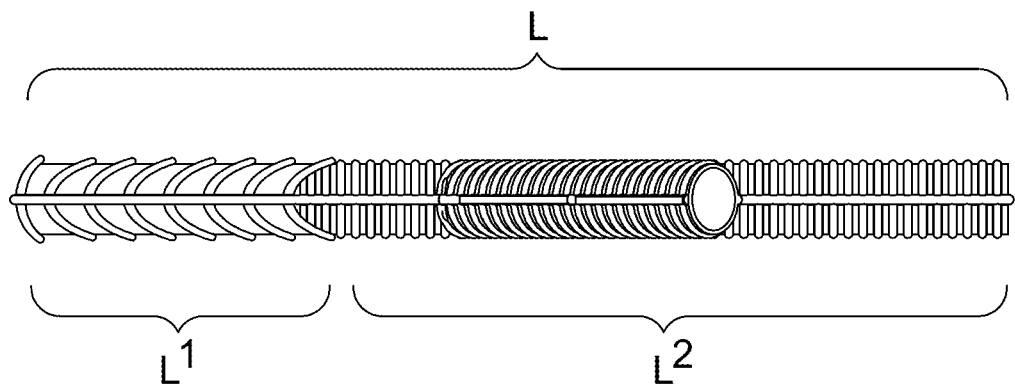
FIG. 5 is a view from above of the implantable tubular body of FIG. 3.
Figure 6:
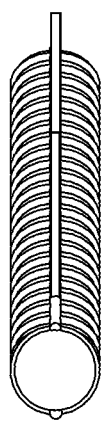
FIG. 6 is an end view of the implantable tubular body of FIG. 3 as viewed lengthwise from the left of FIG. 3.
Figure 7:
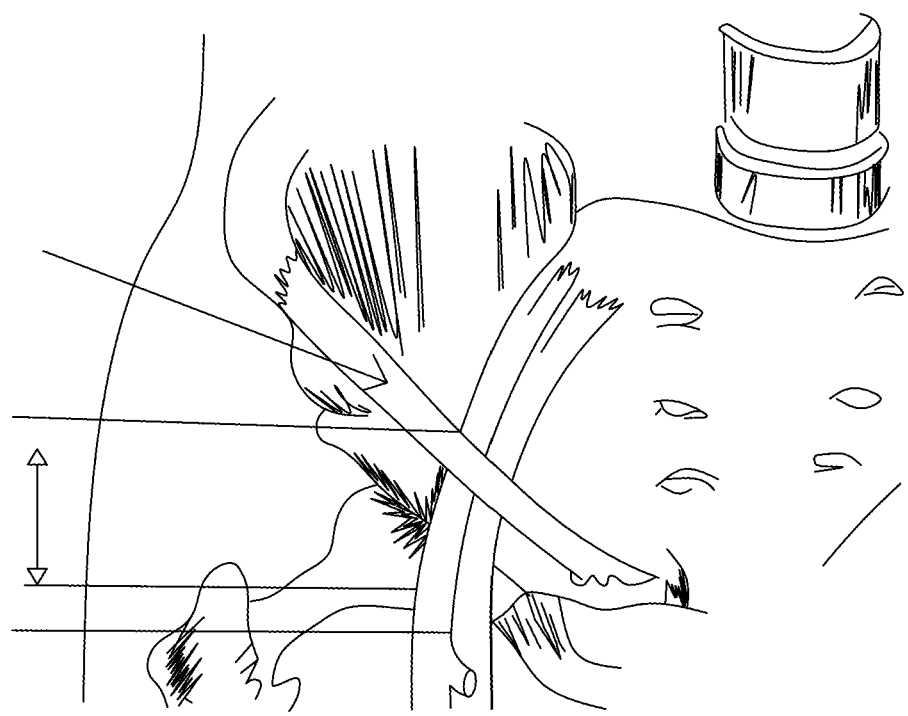
FIG. 7 illustrates schematically an initial step in a surgical procedure to locate a natural vessel, for example the iliac, by reference to the inguinal ligament, which runs from the anterior superior iliac spine to the pubic tubercle.
Figure 8:
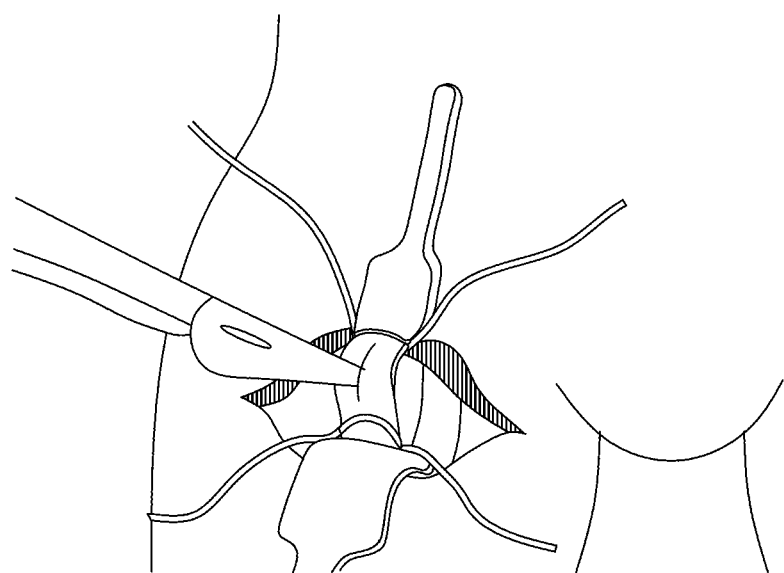
FIG. 8 illustrates schematically a subsequent step in a surgical procedure where an initial surgical incision site is retracted laterally to a surgeon to expose, tie off (by ligature) and make an incision into the natural vessel, for example the iliac, to provide an access point.
Figure 9:
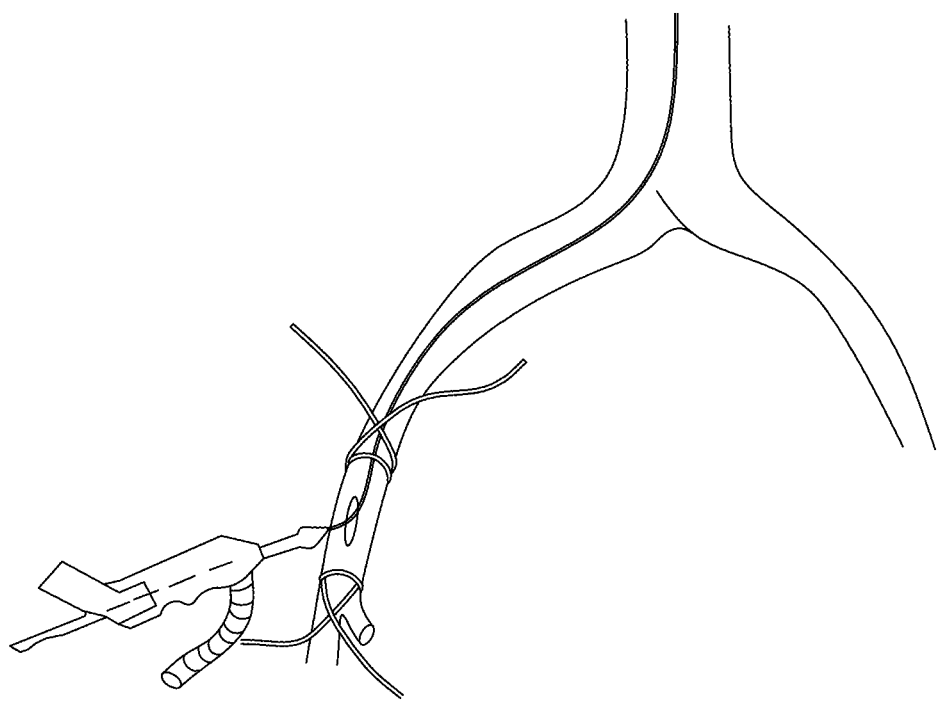
FIG. 9 illustrates schematically, introduction of a guidewire to prepare for introduction of a delivery system.
Figure 10:
FIG. 10 illustrates schematically the application of haemostat clamps, notably to a perfusion branch of a tubular device carried by the delivery system, and the advancing of the delivery system into the natural vessel via the incision access point.

In an embodiment illustrated in FIGS. 3 to 6, an implantable graft, referring first to FIG. 3, comprises a tubular body 31 having a bifurcated (Y) configuration and having a length dimension L comprising a tubular length portion $L^1$ and a further tubular length portion $L^2$. The tubular length portion $L^1$ forms an endovascular section 30 and has a plurality stents 41 which are compressible to a compact form and expandable to support the tubular length $L^1$ in an expanded (dilated) configuration. In use, the endovascular section 30 would be sheathed for delivery into a target natural vessel of the vasculature.

Figure 11:
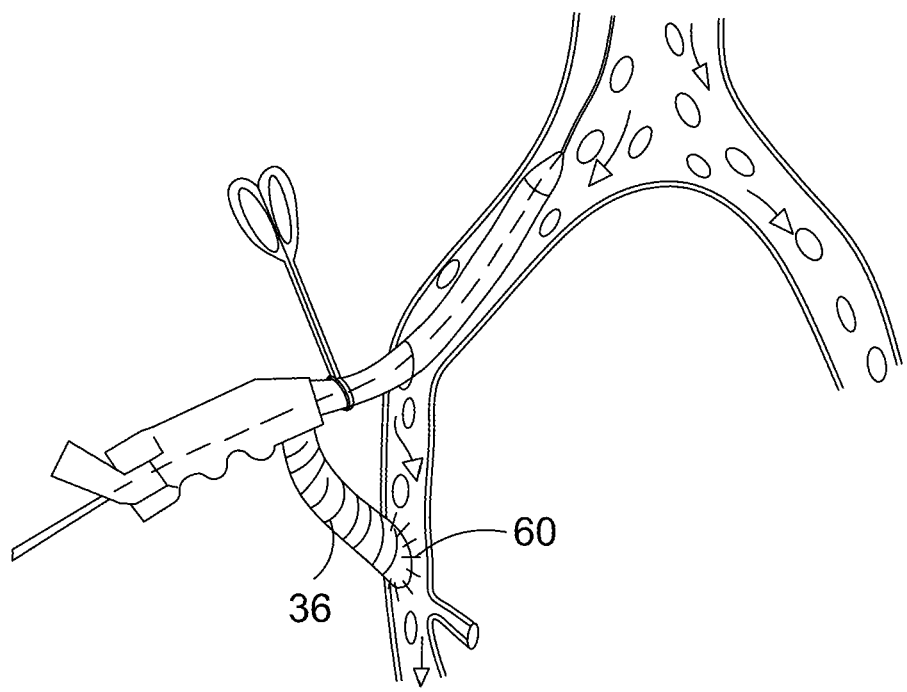
FIG. 11 illustrates schematically the anastomosis of the perfusion branch to the natural vessel.
Figure 12:
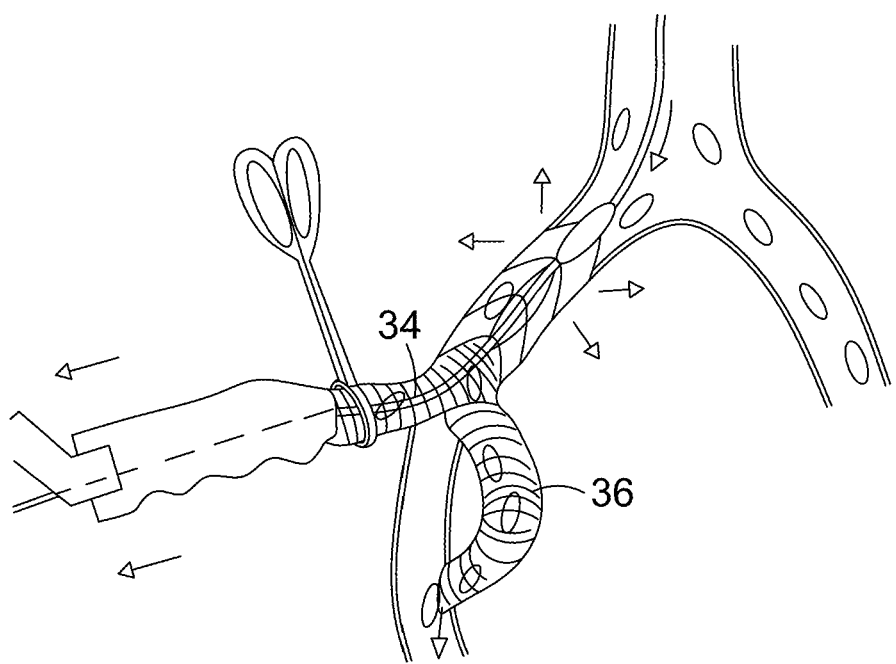
FIG. 12 illustrates schematically, a step in the procedure whereby air is vented from the delivery system via an internal valve associated with a tubular part of the tubular device, and an endo-portion of the tubular device is deployed within the natural vessel during dilation of the latter by means of an integrated balloon carried by the delivery system upon which the tubular device is positioned.
Figure 13:
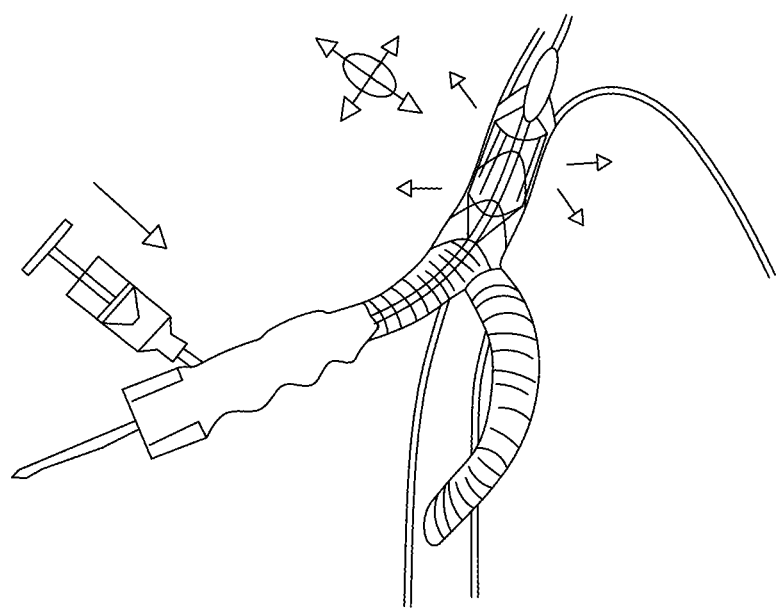
FIG. 13 illustrates schematically the expansion of the deployed tubular device by inflation of the integrated balloon from an external fluid supply device (syringe indicated), after which the balloon can be deflated for removal.
Figure 14:
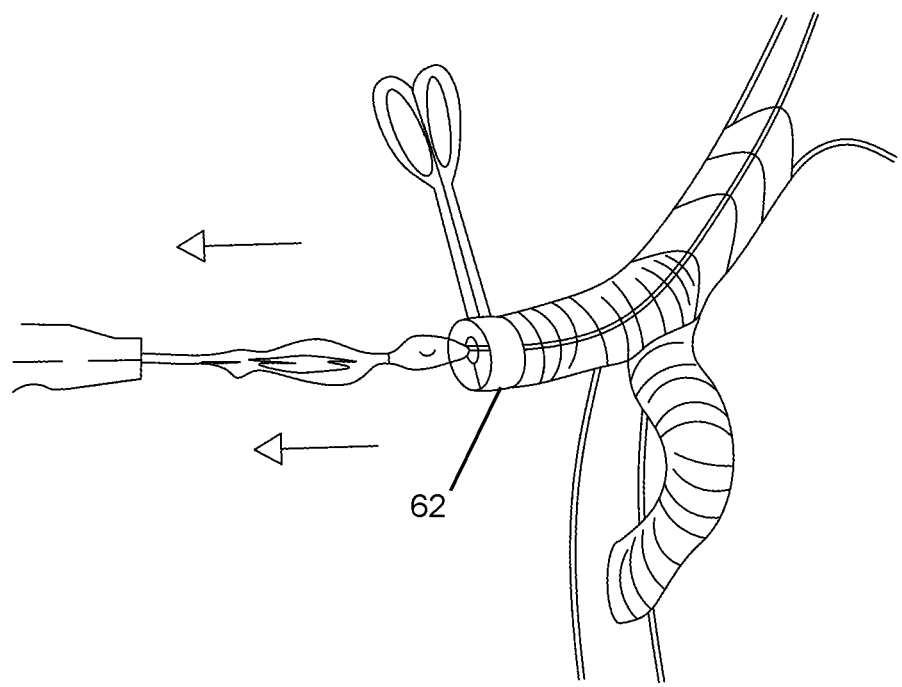
FIG. 14 illustrates schematically the removal of the delivery system with integrated balloon through a valve located within a tubular part of the tubular device.
Figure 15:
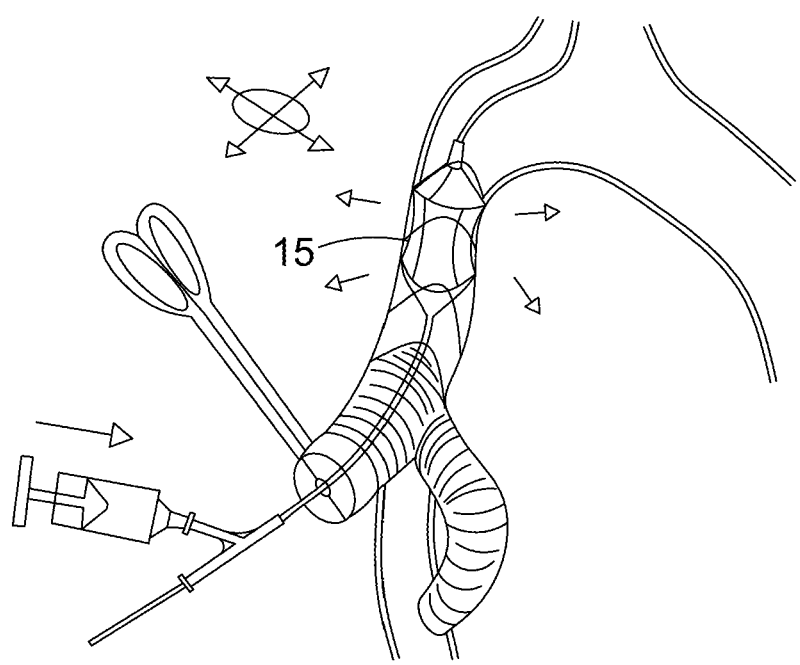
FIG. 15 illustrates schematically the inflation of a bigger balloon inserted through the valve located within the tubular device and subsequent deflation after the tubular device has been expanded to a greater lumen dimension.
Figure 16:
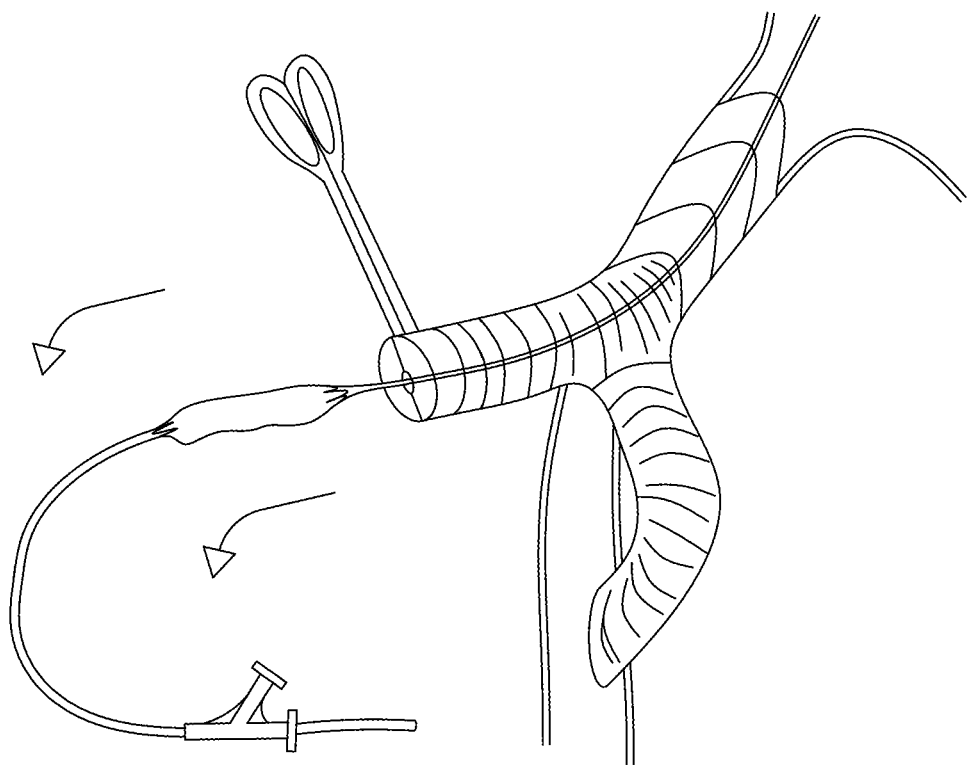
FIG. 16 illustrates schematically the removal of the deflated bigger balloon.
Figure 17:
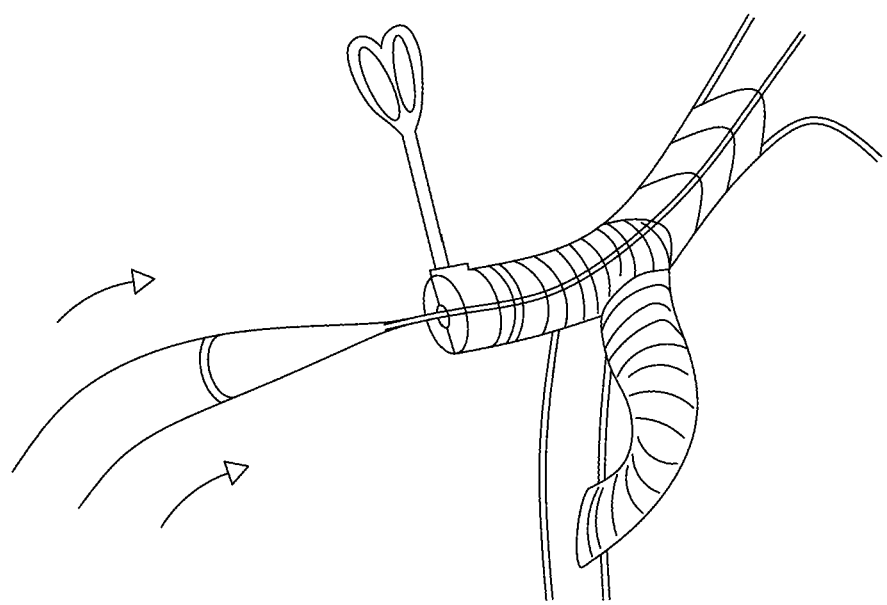
FIG. 17 illustrates schematically the threading of the EVAR system onto the guidewire for subsequent introduction via the valve through the tubular device and onward through the vasculature to a site requiring deployment of an endograft.
Figure 18:
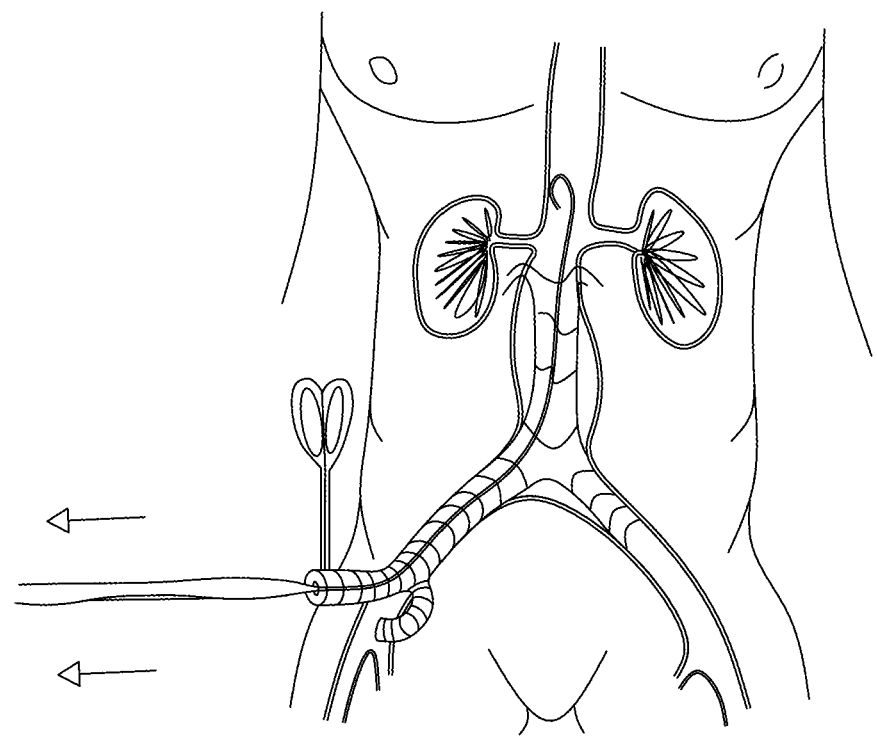
FIG. 18 illustrates schematically the deployed bifurcated graft introduced by the EVAR system which system is retracted (withdrawn)
Figure 19:
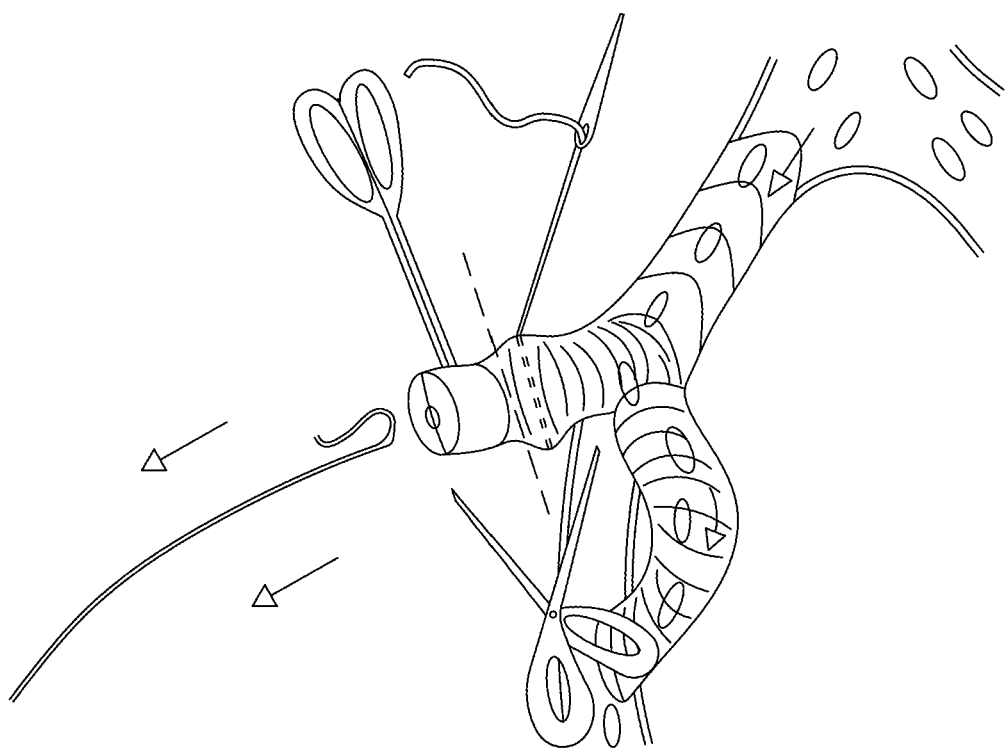
FIG. 19 illustrates schematically the removal of the guidewire, stitching closure of the part of the tubular body through which the delivery system had gain access to the vasculature, such that the valve and excess length of the tubular device can be cut off.
Figure 20:
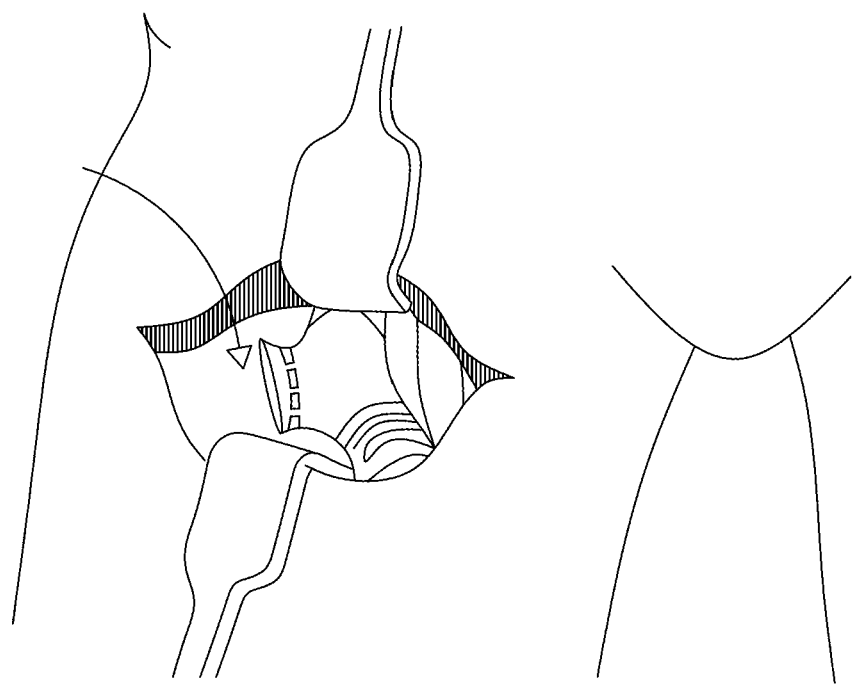
FIG. 20 illustrates schematically a final tubular device placement within the retracted incision site.
Figure 21:
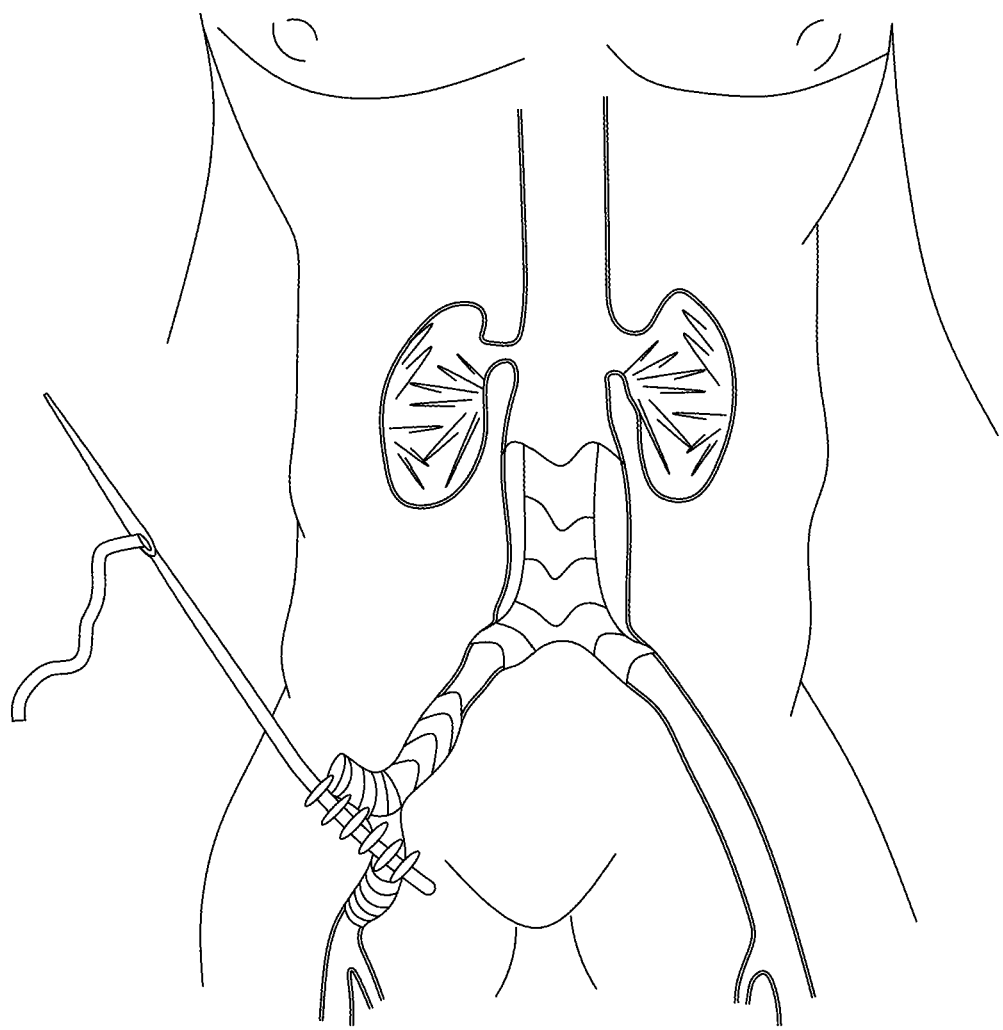
FIG. 21 illustrates schematically the final surgical step of stitching up the incision.

One of the bifurcated limbs serves as a perfusion branch 36 which may be anastomosed to a natural vessel 60 (FIG. 11) in the performance of a surgical procedure.

The other of the bifurcated limbs serves as an access branch 34 for introduction or removal of a delivery system component, and for conducting an EVAR procedure.

At least a portion of the access branch 34 has a trimmable length comprising a series of sections 37, each section having a tab or loop 38 which may be gripped to facilitate trimming of the length of that branch limb of the tubular body 31.

The implantable graft is made of fabric in the form of a collapsible sleeve. The tubular length portion $L^1$ and the further tubular length portion $L^2$ respectively may be made of the same or different fluid-impermeable fabrics selected from physiologically acceptable or benign materials such as a knitted or woven fabric of ePTFE, PTFE or polyester, polyethylene or polypropylene. The fabric may be sealed with a sealant, for example gelatine or collagen.

The endovascular section 30 includes stents 41 which are separate ring stents which are individually attached to the fabric sleeve and configured for final use to support a dilated fabric sleeve as "saddle" shaped stents having peak 42 and valley 43 portions.

Each of the ring stents 41 may be made of continuous loop of resilient material such as stainless steel, or a shape memory metal alloy like nitinol (a nickel-titanium alloy) or high modulus polymers such as polyether ether ketone PEEK or the like, and may be attached to the fabric sleeve by way of sutures, adhesive or heat bonding as appropriate.

Each ring stent 41 may be formed from a shape memory material which may be heat set against the external surface of the endovascular section 30. In the depicted example (FIG. 3), the undulating contour of each ring stent 41 comprises a compressible memory material readily forming two peaks 42 and two valleys 43 to form in use a " " saddle-shaped" ring stent. Use of a continuous loop of multiple windings of nitinol wire is advantageous for this purpose.

Thus the stented endovascular section is self-expanding and can assume a fully open lumen dimension after the target natural vessel is fully dilated by means of the balloon.

In use, referring to FIGS. 7 to 21, which illustrate in "storyboard" format a surgical procedure using the embodiment of FIGS. 3 to 6, the surgical procedure may be conducted as follows.

After preparing the surgical field in accordance with current recommended medical practice, the target natural vessel, for example the iliac, is located by reference to the inguinal ligament, which runs from the anterior superior iliac spine to the pubic tubercle.

Then an appropriate incision is made and retracted to expose the target iliac, which is tied off (by ligature) and an incision is made into the iliac, to provide an access point for insertion of a bifurcated endovascular tubular device including a branch suitable for use for perfusion.

A guidewire is introduced (Seldinger wire technique) into the iliac to prepare for introduction of a delivery system with endovascular tubular device. An endo-section of the latter being threaded and guided into the iliac over the guidewire.

Suitable haemostat clamps are applied to the device including to a perfusion branch of a tubular device carried by the delivery system, and the advancing of the delivery system into the iliac via the incision access point is initiated sufficiently to present the perfusion branch to the iliac at a point remote from the first insertion incision point.

The perfusion branch is then anastomosed to the iliac to complete a perfusion by-pass pathway through the endovascular tubular device.

At this stage in the procedure it is possible to vent air from the delivery system via an internal valve 62 associated with a tubular part of the tubular device, and a stented endo-portion of the tubular device is deployed within the natural vessel that is at least partially dilated by means of an integrated balloon carried by the delivery system upon which the tubular device is positioned.

The expansion of the deployed tubular device proceeds along with inflation of the integrated balloon from an external fluid supply device (e.g. syringe indicated FIG. 13), after which the balloon can be deflated for removal.

The delivery system with integrated balloon is withdrawn through a valve located within a tubular part of the tubular device, leaving the inflated stented endo-portion of the tubular device supporting a dilated portion of the iliac.

Where the dilated portion of the iliac needs to be further dilated, for example, to permit transit of an EVAR system, a larger balloon on another delivery system can be inserted through the valve located within the tubular device and subsequently inflated to further expand the previously inflated stented endo-portion of the tubular device, whereafter the second balloon can deflated and withdrawn on its delivery system leaving the stented endo-portion of the tubular device in a further expanded state to enlarge the already dilated iliac to a greater lumen dimension. The use of further balloons of ever-increasing inflation capacity in repeated steps such as above described may be implemented until the natural vessel is sufficiently dilated or ruptured to allow the endovascular stented tubular body portion $L^1$ to be adequately expanded to permit access for an EVAR system. The tubular device remains implanted as a resident tubular graft substituting for the possibly ruptured iliac vessel and having sufficient lumen dimensions for access to the vasculature beyond the tubular graft implant site in the iliac.

Assuming the iliac has been sufficiently dilated by the successive use of the balloons, the resident expanded tubular device maintains sufficient patency for an EVAR system to be threaded onto the guidewire (Seldinger guidewire technique) for subsequent introduction through the tubular device and onward through the vasculature to a site requiring deployment of an endograft.

The delivery system can be removed and the surgical procedure concluded in accordance with normal good practice.

Figure 22:
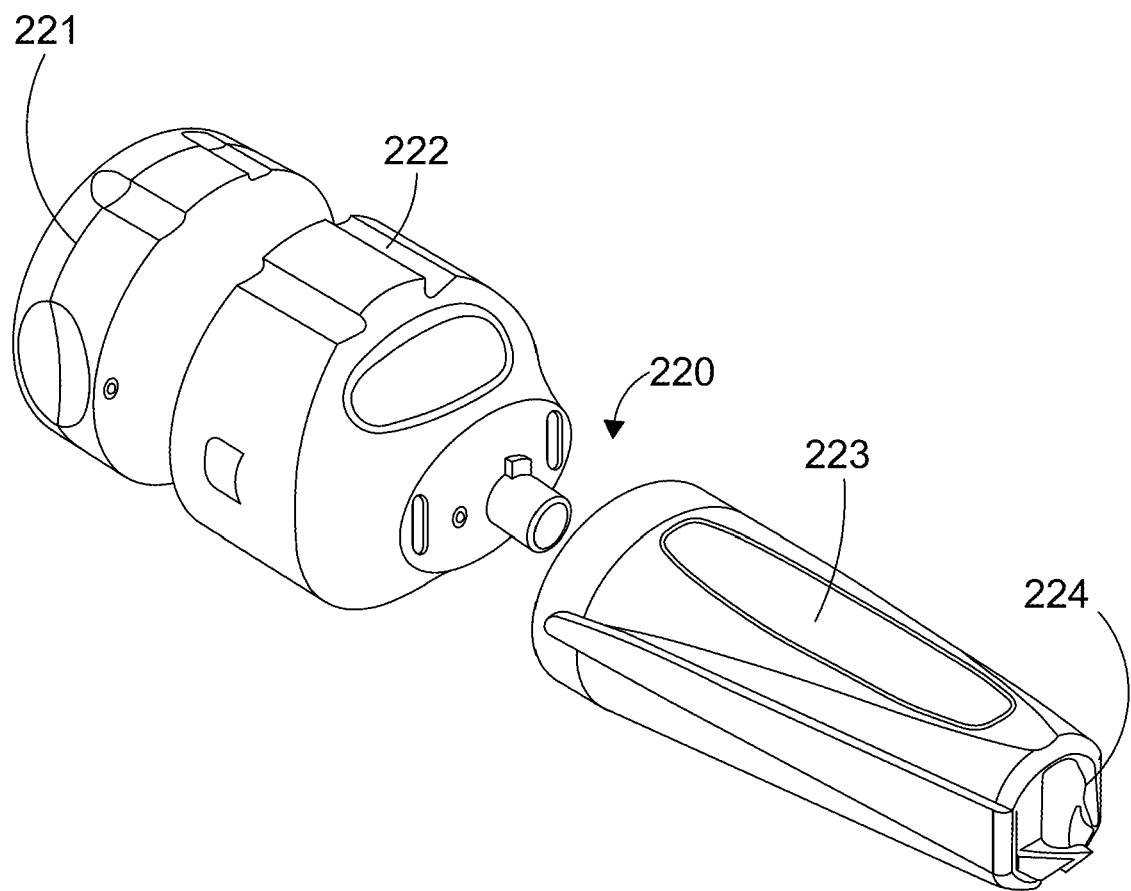
FIG. 22 illustrates handle parts of an embodiment of the delivery system.

Referring to FIG. 22, a delivery system has an operator handle 220 for manipulation and control of the system, of which certain components are shown. The handle 220 is formed in parts and has a length designed to overlie at least a part of a tubular device to be delivered, with a lengthwise axial throughbore, and through which a wire, catheter or flexible or malleable shaft may be passed. The handle parts include, a first handle part 221 for receiving a pull handle strap to be passed through to a removable sheath, a hub 222, and a slotted tapered grip 223. A sheath-slitter device 224 may be incorporated within the handle, optionally upon the hub, but conveniently is presented at the front of the handle 220 at a distal surface of the slotted tapered grip 223.

Figure 23:
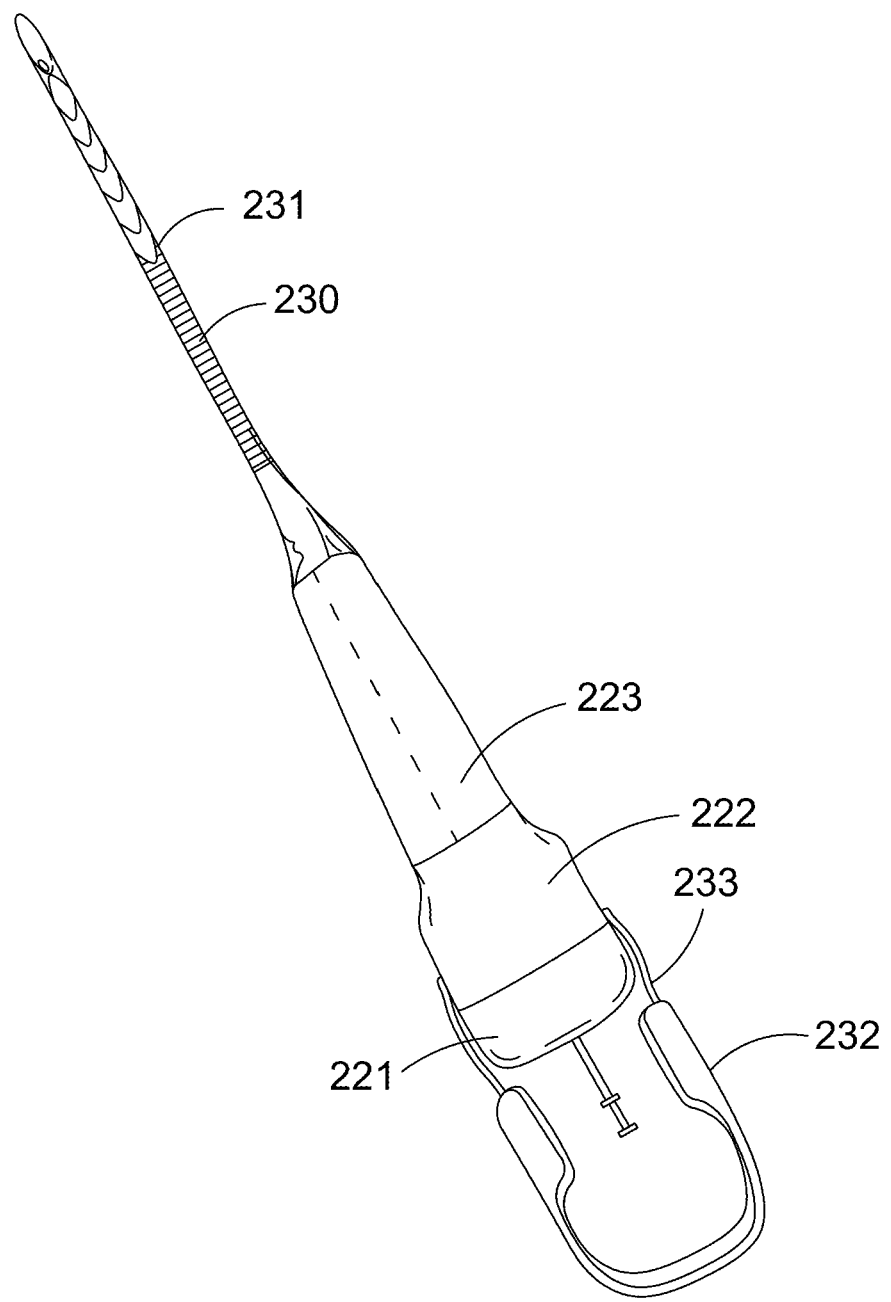
FIG. 23 illustrates an embodiment of the delivery system loaded with a tubular device which is in low profile compact form within a removable sheath.

FIG. 23 illustrates an embodiment of the delivery system loaded with a tubular device 231 which is in a low profile compact form within a removable sheath 230. A U-shaped pull handle 232 is connected by straps 233 through an operator handle 220, to the removable sheath 230. In use an operator can manipulate the delivery system using the operator handle 220, to advance or withdraw the delivery system with respect to an inserted guidewire (Seldinger technique) to position the tubular device 231 within a natural iliac vessel. When the tubular device 231 is suitably positioned, the U-shaped pull handle 232 can be used to retract the sheath 230 to deploy the tubular device 231 within the natural iliac vessel. After an appropriate balloon expansion step, the operator handle 220 can be used to withdraw the inserted parts of the delivery system, including the deflated integrated balloon through a dry-seal/valve (FIG. 14) integrated into an unstented limb of the tubular device.

Figure 24:
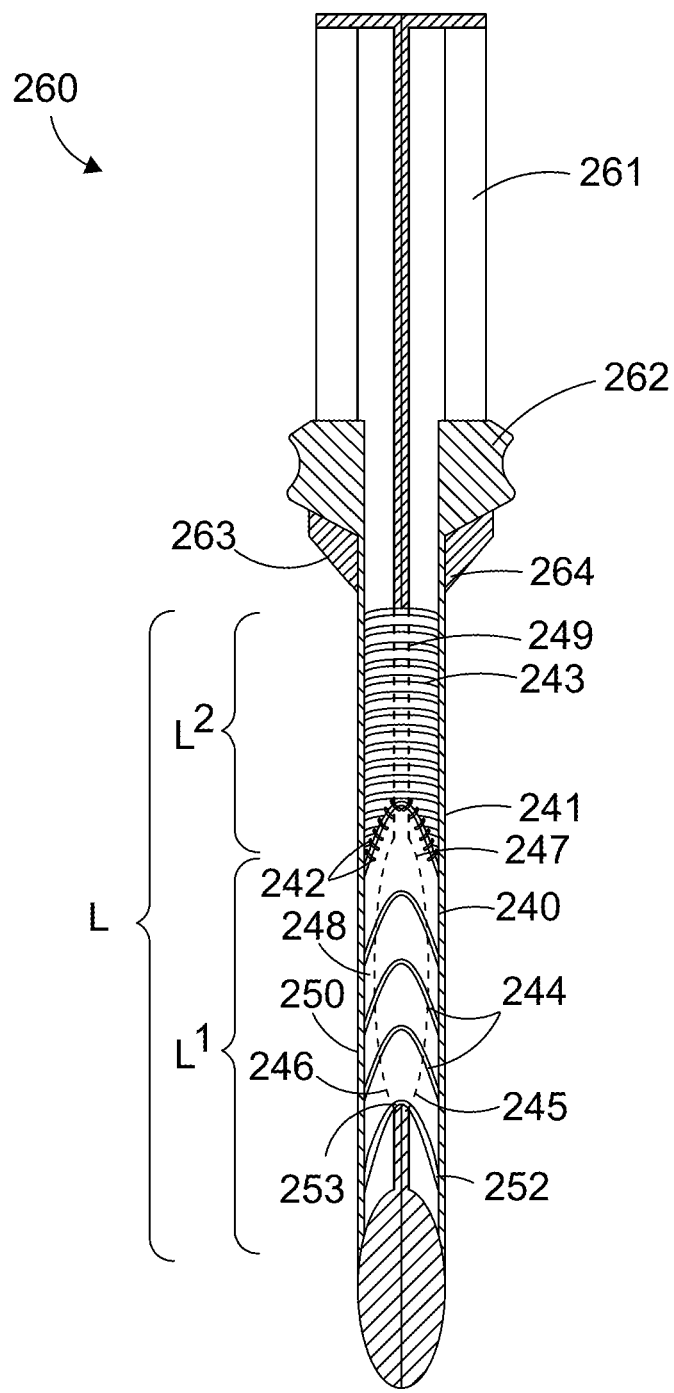
FIG. 24 illustrates a partially cutaway view of an embodiment of the delivery system loaded with a tubular device, and integrated balloon, which are in low profile compact form within a removable sheath.

FIG. 24 illustrates a partial cutaway view of an embodiment of the apparatus including a delivery system loaded with a tubular device 240 and integrated balloon 245 which are configured in a low profile compact form within a removable sheath 241.

The tubular device 240 provides an implantable graft similar to the tubular devices 31, 231 as described above. The tubular device 240 comprises two tubular sections secured together for example by sutures 242 to form a blood-tight seal and forming a hollow tubular body 243 having a length dimension L comprising a tubular length portion L1 and a further tubular length portion L2. The tubular length portion L1 forms an endovascular section 250 and has a plurality of stents 244 which are compressible to a compact form and expandable to support the tubular length L1 in an expanded (dilated) configuration. The compact form can be held for delivery by use of a removable sheath, as depicted. The implantable graft includes the integrated balloon 245 which may expand the endovascular section 250 when the section 250 is unsheathed. The balloon 245, has a collapsible tubular shape with tapering ends. The tubular shape has truncated cone-shaped tapered sections 246, 247 respectively on the distal and proximal ends of a straight tubular profile section 248, which tapered sections 246, 247 are fixed to a tubular element 249 to define therebetween an expansion volume which may exceed the natural volume of the corresponding length of the target natural vessel. The endovascular section 250 includes the stents 244 which are separate ring stents which are individually attached to the fabric sleeve and configured for final use to support a dilated fabric sleeve as "saddle" shaped stents having peak 252 and valley 253 portions.

The delivery system is of the type described with reference to FIG. 23, having an operator handle 260 for manipulation and control of the system. The handle 260 is formed in parts and has a length designed to overlie at least a part of a tubular device to be delivered, with a lengthwise axial throughbore, and through which a wire, catheter or flexible or malleable shaft may be passed. The handle parts include: a first handle part 261 for receiving a pull handle strap to be passed through to a removable sheath, a hub 262, and a slotted tapered grip 263. A sheath-slitter device 264 may be incorporated within the handle 260, optionally upon the hub, but conveniently is presented at the front of the handle 260 at a distal surface of the slotted tapered grip 263.

The use of the embodiment of FIG. 24 is analogous to that described for the embodiment of FIGS. 3-6, and in a surgical procedure as described referring to FIGS. 7 to 21.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A tubular medical system, comprising:
   a) a self-expanding tubular body (31, 243) having a bifurcated configuration that includes,
      i) a stented tubular length portion ($L^1$) that includes self-expanding stents,
      ii) a pair of bifurcated limbs, including
         a. a crimped tubular length portion ($L^2$), the crimped tubular length portion ($L^2$) being secured to the stented tubular length portion ($L^1$),
         b. an access branch (34) at the crimped tubular length portion ($L^2$);
   b) a removable sheath (230, 241) radially constricting the stented tubular length portion ($L^1$); and
   c) a delivery system that includes,
      i) an operator handle (220), including a splitter mechanism (224), through which the removable sheath (230, 241) extends,
      ii) a delivery shaft (249) extending from the operator handle (220), and at least partially within the stented tubular length portion ($L^1$),
      iii) a pull handle (232) at the operator handle (220),
      iv) straps (233) extending from the pull handle (232) to the removable sheath (230, 241), whereby the removable sheath (230, 241) is split by pulling on the pull handle (232),
      v) an integrated balloon (15, 245) within the self-expanding tubular body (31, 243), whereby inflation of the integrated balloon (15, 245) after removal of the removable sheath (230, 241) enables further radial expansion of the stented tubular length portion ($L^1$) of the self-expanding tubular body (31, 243).

2. The tubular medical system of claim 1, wherein the integrated balloon (15, 245) is undersized in relation to a maximum potential expanded dimension of the tubular body (31, 243).

3. The tubular medical system of claim 1, further including an internal valve at the access branch (34).

4. The tubular medical system of claim 3, wherein the valve includes an introducer seal.

5. The tubular medical system of claim 1, wherein the access branch (34) has an outer surface and further includes a plurality of tabs or ribbon loops (38) attached to the outer surface.

6. The tubular medical system of claim 1, wherein the stented tubular length portion ($L^1$) is expandable and includes saddle-shaped ring stents (244), each of which has peak (252) and valley portions (253).

7. The tubular medical system of claim 1, wherein the stented tubular length portion ($L^1$) includes a lining of a polytetrafluoroethylene (PTFE).

8. The tubular medical system of claim 1, wherein the operator handle (220) of the delivery system further includes a hub (222).

9. The tubular medical system of claim 8, wherein the operator handle (220) of the delivery system further includes a grip (223).

10. The tubular medical system of claim 1, wherein the operator handle (220) of the delivery system further includes a grip (223).

\* \* \* \* \*